United States Patent [19]

Taggert et al.

[11] Patent Number: 4,752,356

[45] Date of Patent: Jun. 21, 1988

[54] PAPERMAKING PROCESS

[75] Inventors: Thomas E. Taggert, Jacksonville, Fla.; Jeffrey S. Noe, Newark; Allan M. Springer, Oxford, both of Ohio

[73] Assignee: Miami University, Oxford, Ohio

[21] Appl. No.: 788,771

[22] Filed: Oct. 18, 1985

[51] Int. Cl.$^4$ ............................................. D21F 11/00
[52] U.S. Cl. ................................. 162/198; 162/202; 162/DIG. 11
[58] Field of Search ....... 162/198, DIG. 10, DIG. 11, 162/252, 202, 263; 436/146

[56] References Cited

PUBLICATIONS

McKague et al., "Practical Applications of the Electrokinetics of Papermaking", *TAPPI*, (Dec. 1974), vol. 57, No. 12, pp. 101-103.

W. E. Scott, "A Review of Wet-End Chemistry Process Control Instrumentation", *TAPPI Journal*, (Nov. 1984), vol. 67, No. 11, pp. 72-76.

Stratton et al., "Electrokinetics in Papermaking-A Position Paper".

*Primary Examiner*—Peter Chin
*Attorney, Agent, or Firm*—Frank H. Foster

[57] ABSTRACT

A method for controlling the addition of cationic additive materials to a paper mill slurry used to neutralize the anionic contaminants in a papermaking process is disclosed which utilizes total organic carbon measurements of samples of the slurry as an indicator of the cationic demand of the paper mill slurry. The method of the present invention discloses the discovery that measurements of the total organic carbon taken from filtered samples of the papermaking slurry correlate very well to cationic demand measurements of a papermaking slurry. Therfore, measurements of the total dissolved organic carbon content may be used to determine the desired addition rate of cationic additives in a more convenient and reliable manner than prior control measures. According to the method of the present invention, monitoring of the papermaking slurry by total organic carbon measurements as a cationic additive control parameter provides improved control of such factors as machine drainage and retention.

5 Claims, 5 Drawing Sheets

CLAY/FIBER/FILLER-PLY
CD (lb/ton) vs TOC (ppm C)

| I | X(I) | Y(I) |
|---|---|---|
| 1 | 178.3000 | 21.0000 |
| 2 | 144.0000 | 17.0000 |
| 3 | 129.5000 | 12.6000 |
| 4 | 209.6000 | 28.0000 |
| 5 | 215.6000 | 20.0000 |
| 6 | 199.3000 | 16.0000 |
| 7 | 252.1000 | 40.0000 |
| 8 | 239.0000 | 29.2000 |
| 9 | 225.9000 | 27.2000 |
| 10 | 226.4000 | 36.2000 |
| 11 | 198.1000 | 19.2000 |
| 12 | 155.8000 | 10.8000 |
| 13 | 24.2600 | 2.9500 |
| 14 | 38.8000 | 6.1500 |
| 15 | 3.8380 | 0.2000 |
| 16 | 6.3790 | 1.4000 |
| 17 | 19.0600 | 2.0000 |
| 18 | 27.2400 | 5.0000 |
| 19 | 2.6190 | 0.0000 |
| 20 | 4.4180 | 0.8000 |
| 21 | 6.6080 | 1.2500 |
| 22 | 18.5900 | 1.7000 |
| 23 | 2.9480 | 0.0000 |
| 24 | 24.1200 | 5.2000 |
| 25 | 43.6100 | 12.2000 |
| 26 | 2.5930 | 0.0000 |
| 27 | 1.0640 | 1.0000 |
| 28 | 20.6500 | 2.8500 |
| 29 | 43.1300 | 9.6000 |
| 30 | 1.2930 | 0.0000 |
| 31 | 1.2210 | 0.8000 |
| 32 | 0.8750 | 1.0000 |
| 33 | 21.3200 | 3.0000 |
| 34 | 0.8500 | 0.0000 |

CATIONIC DEMAND vs TOTAL ORGANIC CARBON
ALL EXPERIMENTS EXCEPT FILLER-PLY

PAPERMAKING PROCESS

BACKGROUND

The state of flocculation of a papermaking slurry is very important to the runnability of that slurry on a paper machine. The state of flocculation is affected by both mechanical factors and chemical factors. The mechanical factors are usually optimized as best they can be and then chemical additives are utilized to control the state of flocculation. The state of flocculation influences the machine drainage, response to vacuum, retention, pressing and drying conditions. These factors in turn influence the strength and optical properties of the sheet. Two major non-mechanical factors affecting additive performance are the state of the electrokenetic charge in the system and the quantity of fine solids present. The materials which affect these factors have often been referred to as "anionic trash". Zeta potential has been used to monitor the state of charge present in the system. This measurement, although conceptually correct, is difficult to obtain on an online basis in a paper mill. Sensors have been developed for online usage but have not been widely applied. The Zeta potential measurement only gives magnitude of charge and not the total quantity of charge in the system. To speak to this need the colloid titration technique has been developed and instrumented. The technique is proposed as a means to control additive addition rates in the papermaking system. A current study has shown this technique to have limited value. A better technique is to monitor the cationic demand of the papermaking slurry. This approach is used in an off-line mode of operation by many chemical supplier companies. This approach conceptually is correct but suffers the same problems of measurement difficulties as the Zeta potential since it uses Zeta potential to determine its end point and is relatively cumbersome and time-consuming to employ in an effective on-line mode.

Stricter governmental requirements for controlling the contaminants from papermaking effluents in additon to attrative cost saving potential has led the paper industry toward increasing degrees of closure of the papermaking process and white water re-use via recycling. However, such a practice leads to an increase in the build-up of organic and inorganic contaminants and fines in the recycle white water.

The anionic organic moieties in the papermaking slurry complete with the filler and fiber constituents of the papermaking stock for adsorption of the costly cationic chemicals used to influence the retention, drainage and other important factors in the papermaking process.

Under present practice, the use of costly chemical additives has proceeded on a trial and error basis to attempt to improve retention and drainage in papermaking processes. This practice has proven only minimally satisfactory because a reliable monitoring and control strategy has not been devised which offers a convenient and reliable indication of the parameters which influence cationic demand of the papermaking slurry and hence the control of the addition rate of cationic materials used to neutralize anionic contaminants for more effective use of cationic and anionic additives.

Since system upsets can easily occur in paper mill operations, lack of a relatively convenient and sufficiently reliable control parameter often leads to errors in the necessary chemical addition rate and failure to achieve the desired quality of product or a significant increase in costs or both. This is true irrespective of the degree of recycling of the white water, although it becomes more significant as the system is closed and the degree of recycling increases above 80% of so.

The current procedure of utilizing Zeta potential measurements, colloidal titration techniques or direct off-line cationic demand monitoring has not provided a satisfactory solution to the problem of achieving satisfactory control techniques necessary to maximize the desirable economic and evironmental results in papermaking processes.

SUMMARY OF INVENTION

The present invention relates generally to paper board and papermaking processes and particularly to an improved process which utilizes total organic carbon measurements of the papermaking slurry to control the addition rates of cationic chemicals necessary to obtain the desired level of charge neutralization of the slurry prior to introduction into the head box of papermaking machines.

Total organic carbon, hereinafter referred to as TOC, as used herein is defined as measurements or the analysis of the dissolved, oxidizeable carbonaceous compounds found in the filtrate of a filtered sample of a papermaking slurry and any of the same type of materials in collidial form which may pass through the filter and are present in the filtrate.

At present, cationic demand measurements appear to be the most reliable indicator of the total quantity of electrokenetic charge of the papermaking slurry as compared to other prior measurements such as Zeta potential and the like and therefore a very important parameter to use to control polymer addition rates.

The invention revolves around the surprising discovery that TOC measurements based upon filtered samples of the papermaking slurry correlate very well with cationic demand measurements of the slurry and therefore may be used as a control parameter for the rate of addition of conventional cationic polymers used to neutralize the anionic contaminants in the slurry.

In view of this unexpected and surprising discovery, TOC measurements may be advantageously employed in a more reliable and more convenient manner to monitor and control the very important addition rates of cationic materials in a papermaking process to achieve greater efficiency and aid in maintaining the desired level of quality of the resulting paper product as compared to prior methods and means.

Additionally, the nature of measuring the TOC content of a given papermaking slurry lends itself more conveniently to the development of on-line instrumentation within a paper mill as compared to cationic demand measurements which are a reliable indicator but more cumbersome and difficult to employ in a highly useful manner.

Implementation of the discovery of the present invention provides a base to develop an essentially fully automatic control system wherein other desired measurements of system variables can be exploited to bring the evolving increase of recycled white water in the papermaking industry to its fullest and mos efficient development.

In accordance with the present invention, TOC measurements would be selectively monitored in the incoming papermaking slurry coming from the thick stock system at a point prior to the stock preparation and blending system. A baseline value of the incoming slurry would first be established to check the correlation with cationic demand measurements of the same slurry such that the correlation could be used throughout continuation of the processing.

Then the addition of conventionally used cationic polymer materials would be controlled in response to the measurements of TOC. In addition to measurements of TOC, it would be preferred to also monitor the specific conductance of the incoming slurry as an indication of the inorganic content of the slurry. Recent studies at Miami University (Ohio) have shown that a rise in the inorganic content of the slurry tend to lower the cationic demand and are reflected by a decrease in TOC.

Further, in any such process, a conventional retention meter, fine solids sensor and ash sensor could be advantageously employed to monitor these variables in the system to provide fuller control of the chemical additives necessary to obtain desired retention and drainage levels.

OBJECTS

It is therefore a primary object to provide an improved papermaking process which incorporates monitoring the charge of a papermaking slurry by a novel and more convenient control parameter to adjust the addition of cationic materials to the paper stock and to improve control of such important factors of machine drainage, response to vacuum and retention, for example.

It is another object of the present invention to provide a method for indirectly, but reliably, determining the rate of polymer addition to a papermaking slurry by employing TOC measurements which are more reliable indicators of the total quantity of the charge in the slurry than measurements of either Zeta potential or those obtained by collodial titration methods.

It is a further object of the present invention to provide an improved papermaking process wherein TOC analysis of a slurry sample is used to control polymer addition to the slurry in a manner which reduces loss of costly raw materials, increases the economic benefits of water recycle/reuse, and provides the potential for increased production rates to be achieved while lowering energy consumption.

Further objects and advantages of the present invention will be apparent from the following description, reference being had to the accompanying drawings wherein a preferred form of embodiment of the invention is clearly shown.

IN THE DRAWINGS

FIG. 1 is a diagrammatic view of a simplified papermaking process employing the teachings of the present invention;

FIG. 2 is a diagrammatic view of a typical papermaking process including proposed monitoring and control features in addition to the TOC measurements used in accordance with the present invention; and FIG. 3 is a graphical representation of the data collected to establish a typical baseline value for the correlation of cationic demand versus TOC illustrating a reliable linear relationship between these parameters of a papermaking slurry.

FIG. 4 is a graphical representation of experimental data wherein cationic demand is plotted against total organic carbon measurements for selected fiber and clay systems; and FIG. 5 is another graphical representation similar to FIGS. 3 and 4 wherein a summary of all points generated in all experimental work connected with the present invention, with the exception of certain filler-ply experiments, is shown.

DETAILED DESCRIPTION

Figure 1:
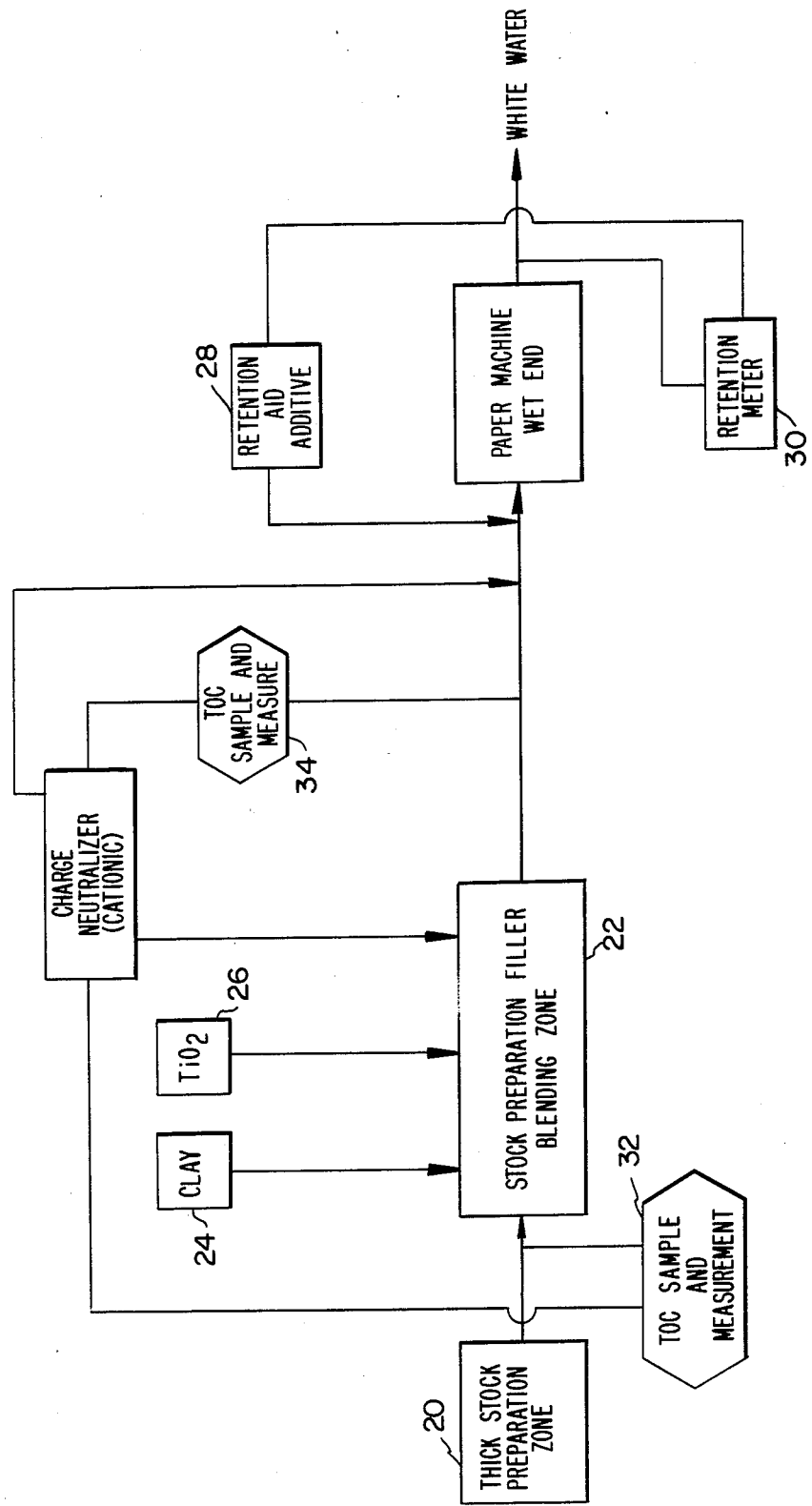

FIG. 1 is a diagrammatic view representing a relatively simplified papermaking process which incorporates the novel concept of TOC monitoring for control of the addition of cationic chemical employed in a typical papermaking process.

In such systems, although equipment and techniques may vary, typically the pulp materials which are to be used in making of the paper mill slurry are first processed in what is referred to as a "thick stock area" prior to further dilution with water to "thin" the stock. This water may be "fresh" (previously unused), or may include a given proportion, up to 100 percent, of recycled "white water". "White water" refers to the effluent liquid which leaves the paper making machine at the so-called "wet end" of the process. Such a process is well-known in the art and therefore a detailed description is not necessary for purposes of understanding the present invention.

Environmental regulations require that this white water be treated to reduce or eliminate undesirable contamination prior to release into the environment. Such regulations have also encouraged the trend to develop increased use of recycled white water in the process along with certain economic incentives, including recovery and re-use of raw materials used in the process and reduction of costly waste-water treatment.

The desired level of control of such processes has been relatively difficult in view of the variables inherent therein which are introduced by both mechanical and chemical factors. The mechanical factors may be improved to an optimum by appropriate design within the limits of the high initial cost of equipment, however, this would not be sufficient to account for the changing chemical environment during the process to maintain the desired level of efficient operation. This is particularly true with regard to control of the important factors of first pass retention and machine drainage. Other important parameters include response to vacuum and pressing dryness as well as strength and optical qualities of the final product in certain applications. However, the first pass retention level and machine drainage are two of the common parameters which determine the effectiveness and efficiency of any medium to high speed papermaking process.

For some time the industry has known that electrokenetic charge is a very important parameter to consider in the chemistry of papermaking. Prior attempts to utilize Zeta potential measurements have not prove to be sufficient to offer a satisfactory solution to the wet-end chemistry phenomena which occur.

While cationic demand measurements, which are determined by titration of the papermaking slurry to zero mobility by addition of a cationic polymer, represent reliable and useful indications of the total quantity of the charge in the system, it is so cumbersome and time-consuming as to be inconvenient for use under the dynamic conditions of commerical papermaking.

In accordance with the present invention, it has been discovered that TOC measurements can serve as a very reliable measure of the cationic demand of a papermaking process and therefore can serve as a reliable monitor for controlling the addition level of the cationic polymers used to neutralize the slurry prior to delivery to the papermaking machine.

As shown in FIG. 1, pulp formed into thick stock at 20 is delivered to a stock preparation and blending area 22. Water, fresh or recycled, not shown, would be used to thin the stock prior to addition of typical filler and sizing materials, such as clay at 24 and titanium oxide at 26. Depending upon the nature of the raw materials initially used and the specifications of the final paper product, other materials may be conventionally used without departing from the spirit of the present invention.

In the stock preparation area of the process, a charge neutralization chemical is conventionally added to reduce the total anionic charge in the papermaking slurry to a given level as indicated at 27.

It is well-known that cationic additives are useful and necessary to provide improved retention and machine drainage. The anionic contaminants in a papermaking slurry include the dissolved carbonaceous compounds derived from the wood components used and tend to block the bonding sites on the fibers and fillers to the detriment of the flocculation desired in the process. These anionic contaminants are referred to in the industry as "anionic trash".

Generally, the charge-neutralizing polymers preferred in the papermaking industry are those having a relatively low molecular weight, a high charge density and are cationically charged. Their main function is to control the dissolved and fine solid anionic components in the papermaking slurry to effectively neutralize the system to a desired level. Examples of such polymers include quaternay polyamines, polyethylenimines, and aluminum sulfate or alum.

Some papermaking systems employ dual polymer additive strategy. After addition of the cationic charge-neutralizer to the slurry, a retention aid is added such as indicated at 28 in FIG. 1. The most prevalent commercial anionic polymers which aid retention can be classified into two main categories. The first includes those which are co-polmerized with a given quantity of acrylic acid. The second includes those whose anionic character is derived from the hydrolysis of a specific number of amide groups in a polyacrylamide backbone.

These anionic polymers are characterized by having a relatively very high molecular weight and a low charge density.

After addition of the anionic polymer retention aid, the treated papermaking slurry enters the conventional papermaking machine 36 wherein it is formed on a moving screen into the desired paper product. Typically, the percent of solids in this slurry is low and the fibers, fillers and fines are matted on the screen to form a continuous sheet. Solid concentrations typically may be approximately 1% or so with the remainder being liquid. Much of the water in the slurry is drawn through the screen. This effluent, referred to as white water, is either treated for release into the environment as waste water or recycled depending upon the design of the system. The retained solids matted on the screen to form the paper product are then pressed and dried prior to being wound upon rollers or the like.

A conventional retention measuring means 30 may be used to monitor the percentage of solids in the slurry entering the head box or inlet end of the papermaking machine versus the solids in the outlet water to control the rate of anionic polymer addition such as indicated at 28 in response to maintaining a desired level of retention of solids.

The prior description generally applies to most papermaking processes, except these prior processes have employed a more or less trial and error method to determine the given level of the anionic polymer required to provide the desired neutralization of the anionic charge in the slurry. Frequently, this has led to many problems due to system upsets from several sources in the dynamic changing chemical requirements in the process.

In accordance with the present invention, TOC measurements, indicated at 32, are selectively taken of the incoming slurry from the thick stock area to the stock preparation and blending system. These measurements may be used to control the release of the charge neutralization chemical to the blending system. In accordance with the TOC measurement, any change in the TOC measurement would dictate a corresponding change in the addition rate of the cationic polymer used to obtain the desired level of neutralization which is illustrated by line 33.

Preferably, a second TOC measurement 34 would be taken at the outlet of the stock preparation and blending system to be assured the proper state of neutralization was accomplished and to adjust that level with further additive if required. After this adjustment any anionic retention aid agent made be added prior to introduction to the paper machine.

Figure 3:
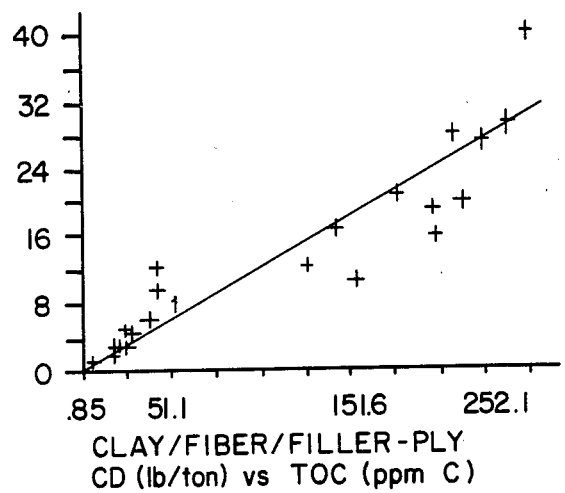

For each particular papermaking system, a baseline value of TOC versus cationic demand may need to be established for the particular papermaking slurry. This may be accomplished by plotting corresponding measurements of TOC versus cationic demand, such as illustrated in FIG. 3, from samples of the thick stock. In this example, cationic demand in pounds per ton is plotted against TOC in parts per million of carbon as detefmined from a representative papermaking slurry.

The slope of the linear relationship may prove to be relatively constant for many typical commercial slurries, however, further testing and evaluation would be needed on a wider range of basis of samples to confirm such a conclusion. However, in this instance, the baseline value for zero cationic demand corresponds to a TOC measurement of 0.85 ppm.

The basic tests and experiments establishing the correlation between cationic demand and TOC measurements are described in greater detail later herein.

Figure 4:
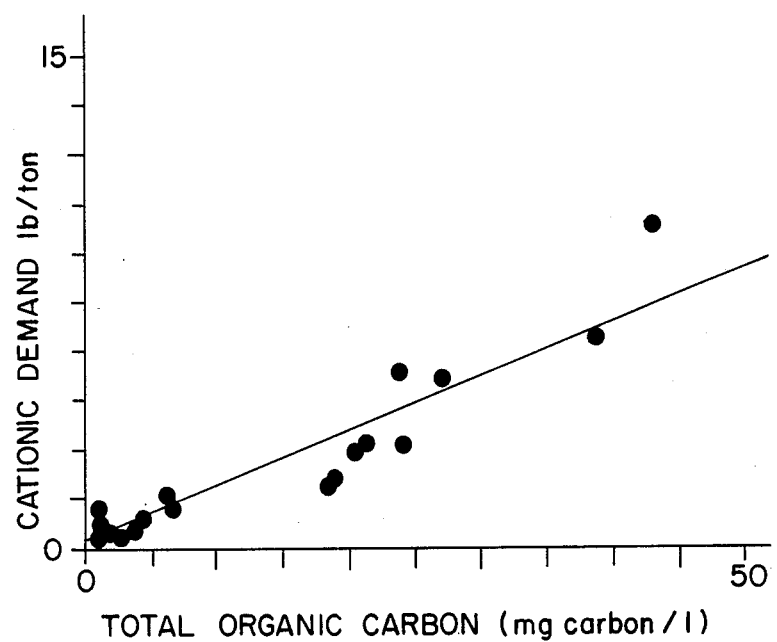
Figure 5:
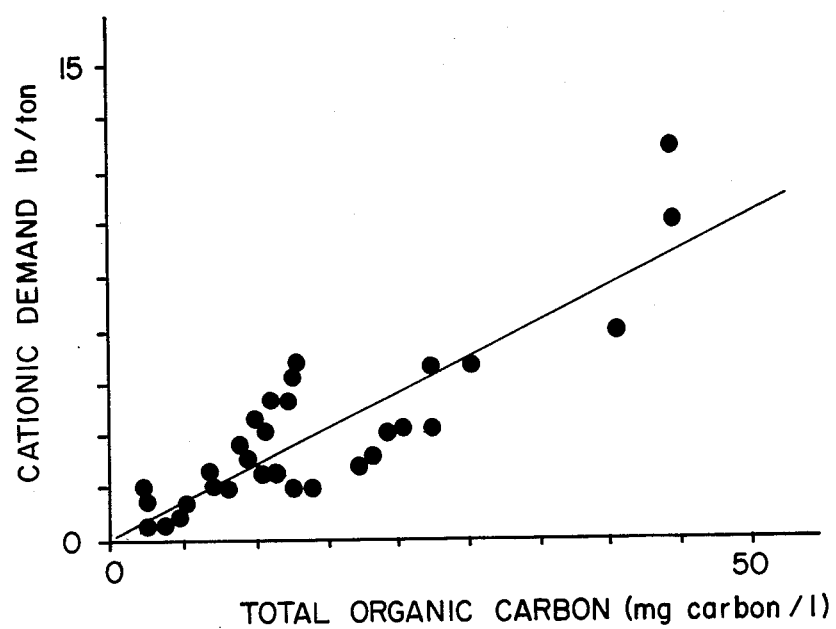

These tests were conducted using several different papermaking variables. Initial investigation revealed that the TOC measurements varied with changes in pH, dissolved inorganics, and with different levels of beating of the pulp fibers. In all these instances, a direct linear correlation was established for cationic demand measurements versus TOC measurements. In the slurries examined an addition rate of one pound of cationic polymer (polyamine) per ton of slurry for each 5 mg increase in organic carbon was established as shown in FIG. 4.

While TOC analysis is a well-known technique, its previous use have been limited to merely determine the level of dissolved organic carbon in a solution. It has also been recognized that increased levels of dissloved organics, which are anionic in character, would cause an increase in cationic demand of a slurry. However, it has never been recognized or expected by those skilled in the art that in a papermaking slurry, that other variables in the slurry heretofore having an unknown relationship to TOC would effect TOC measurements in a linear correlation to the cationic demand of the slurry.

For example, increases in the dissolved inorganics typically present in papermaking slurries were found to lower both the cationic demand and the TOC measurement.

In the same manner, it was discovered that an increase in the concentration level of kaolin clay filler to a slurry containing unbleached softwood kraft pulp at constant consistency and pH showed that a strong linear correlation between cationic demand and TOC existed. In this instance, however, the relationship was inverse. When the filler concentration increased, the TOC measurement was lowered as cationic demand increased.

The very thrust of the present invention resides in this discovery which clearly indicates that the analysis of the dissolved organic carbon content in the papermaking slurry or in the white water recycle provides much more information than merely the level of the oxidezeable carbonaceous components present. It provides a more convenient and readily obtainable parameter to use to control the polymer addition rates to the papermaking process which in turn strongly affect the retention of solids and machine drainage rates obtained in the papermaking process.

Further, improved control of the necessary level of cationic polymer also leads to more effective and efficient use of anionic polymer additives for improved retention and drainage results. A conventional TOC analyzer, known by the tradename, DOHRMAN DC-80, was used to detemine TOC levels. This instrument is based upon a chemical oxidation determination using an ultra-violet promoted persulfate oxidation system followed by infrared detection to determine organic carbon levels. Samples were first filtered to remove solids and the filtrate was analyzed for organic carbon values. The pH was adjusted prior to the organic analysis to remove any inorganic carbon compounds from the measurement.

It should be readily apparent that use of the TOC measurement in accordance with the teachings herein become increasingly valuable in processes having a high level of closure and recycle a greater percentage of the white water effluent. Previous studies have shown that that dissolved contaminants in such recycle systems increase greatly as the percentage of recycling increases.

As the dissolved organics and inorganics, as well as the non-soluble fines increase, the degree of contol of the process variables becomes increasingly important to maintain desired production rates and product quality. In view of the past difficulties in obtaining reliable control information based upon Zeta potential analysis and colloid titration, and the inherent difficulty of automating direct on-line cationic demand measurements, the discovery of the unexpected relationship beteen TOC analysis and cationic demand is a truly drammatic step forward in the art toward achieving a reliable control parameter for adjusting the chemical retention aid addition rates in papermaking processes.

Figure 2:
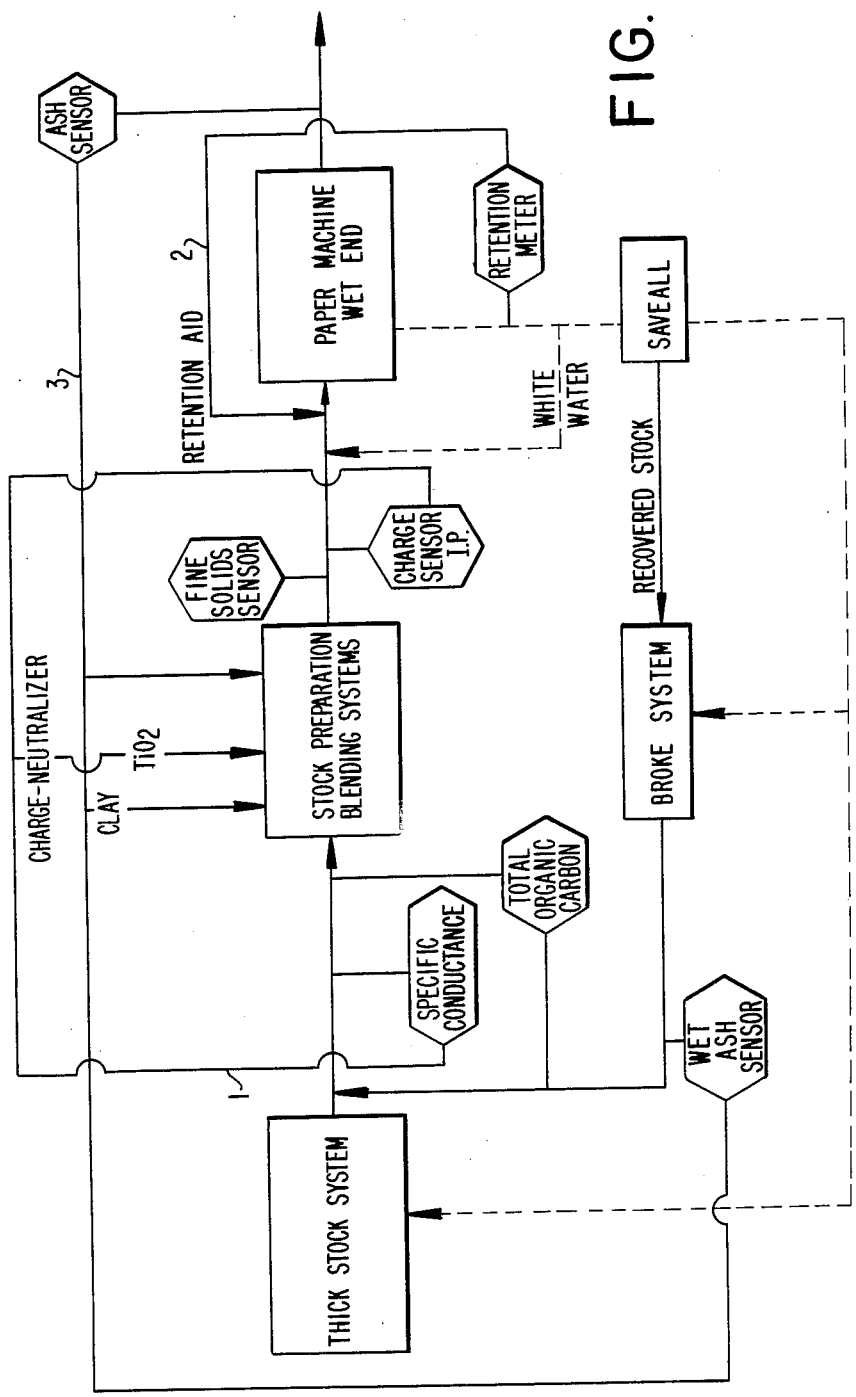

FIG. 2 illustrates, by way of example, a proposed retention and drainage control strategy for a papermaking process which utilizes TOC analysis to control the addition of cationic neutralization agents as well as utilizing other process variable measuring means.

In accordance with this strategy, on-line instrumentation would be developed to essentially automate the control of the process variables. Previously published studies based upon work done at Miami University of Ohio have developed background data which leads to the conclusions forming the basis for this control strategy. The continuous monitoring of the level of contaminants and key process responses and the automatic adjustments of addition control agents in response to the monitored variables would produce many benefits such as:

1. Reduced loss of high cost materials such as titanium dioxide, synthetic size, etc.
2. Increased dewatering on the paper machine leading to a lower water content sheet to the press section (lesser energy requirement in the dryer section).
3. Potential increased machine speeds due to increased drainage rates.
4. Improved paper machine runnability and product properties.
5. Increased water reuse potential which can result in energy and raw material savings.

Three major generalizations can be drawn from the extensive amount of research aimed at elucidating wet-end chemistry mechanisms and fundamental knowledge. These serve as the major basis of a first-pass retention control strategy:

1. The wet-end chemistry performance of most additives and components is highly dependent on the level of first-pass retention achieved.
2. On medium to high speed paper machines, retention said addition is necessary to achieve acceptable first-pass retention levels.
3. The effectiveness of cationic additives is greatly impaired due to interference by dissolved and collodial anionic substances in the wet-end.

The proposed retention and drainage control strategy consists of three main control loops. The first loop measures and neutralizes the organic derived contaminants on the thick stock side of the stock preparation area. Total organic carbon measurements serve as a measure of the cationic demand of the system. Based on the levels detected, a cationic charge neutralizing additive of low molecular weight and high charge density is added to counteract the deterimental organic effects. This amount will be slightly affected by the level of dissolved inorganic material present since these cationic species will react with the negatively charged organics. Specific conductance measurements serve to quantify the level of dissolved inorganic. In theory, as the furnish exits the stock preparation area, the total charge of the system is checked to determine if the organics are sufficiently neutralized to the desired level.

In the second loop, the first-pass retention performance is measured, and the high molecular weight retention aid addition rate is adjusted if a change in retention is necessary. This is to achieve a targeted uniform retention level. A retention value that correlates with first-pass retention can be derived with the M/K retention meter. The adjustment of drainage rates and couch dryness levels would be controlled by this additive, also. Information about the mass of incoming fine solids (filler, pulp, and broke fines) from the stock preparation area is also known and fed forward to this loop.

The third loop illustrated in the diagram monitors the level of filler retention in both the final sheet an in the recycled broke recovery system. This information is fed back so as to adjust the flow rates of mineral fillers, such as clay and $TiO_2$, accordingly in the stock preparation area.

Not illustrated in the diagram, but quite desirable, is a feedback loop which relays information concerning such properties as the optical and strenth characteristics of the paper to some type of process control computer. This information would include measurements of opacity, brightness, strength, etc., so that product specifications would remain acceptable.

In short, a first-pass retention and drainage control strategy could be implemented with relatively few on-line sensors. However, sensors which are currently commercially available are those which measure total charge of the system, process stream fines levels, and wet ash levels in the system. Given the future demands required in the paper machine wet end from alkaline papermaking and the increased filler loading levels, higher machine speeds, lower basis weights, white water recycle, etc., the industry needs to take a stronger approach toward this type of additional on-line process control strategy.

It should be noted that the charge sensor indicated is a zeta potential measurement, however, this could also be preferably replaced with a TOC measurement.

Current work at Miami Univeristy of Ohio to automate an on-line TOC monitoring system is showing significant progress. However, based upon the current practices, off-line TOC determinations still offer significant improvement to provide control data for cationic addition rates to improve papermaking processing compared to prior and current control means.

At this time, and forall practical purposes, it appears that cationic demand is the best parameter of the total quantity of charge in a papermaking system.

In view of the foregoing description, it should be readily apparent that the surprising and unexpected correlation between TOC measurements and cationic demand measurements of papermaking slurries in response to variables heretofore having unknown relationship to these two parameters represents a very drammatic step forward to improving the process of papermaking.

We claim:

1. In a papermaking process of the type having a thick stock preparation zone communicated to a stock preparation and filler blending zone for preparing a papermaking slurry to be delivered to the inlet of the paper machine for making a finished paper sheet product, the combination of the steps of:
   (a) sampling the papermaking slurry communicated from the thick stock preparation zone to the stock preparation and filler blending zone;
   (b) filtering the solids from the sample obtained in step (a) and collecting the filtrate;
   (c) measuring the TOC content of said filtrate obtained in step (b);
   (d) adding an electrokinetic charge neutralization agent to the paper mill slurry prepared in the stock preparation and filler blending zone at a rate responsive to the TOC value obtained in step (c) corresponding to obtaining a predetermined level of electrokinetic charge of the slurry introduced to the paper machine for making a final pape product;
   (e) communicating the papermaking slurry neutralized in accordance to step (d) to a conventional paper machine.
   (f) repeating steps (a-d) as required to maintain a given level of neutralization of the charge of the paper slurry communicated to the paper machine.

2. A process as described in claim 1 including the step of:
   (g) sampling the papermaking slurry exiting the stock preparation and filler blending area prior to delivery to the paper machine and repeating steps (b) and (c);
   (h) adjusting the level of charge of the papermaking slurry by adjusting the addition rate of the charge neutralization agent to the slurry responsive to the TOC measurement obtained in step (g).

3. The process defined in claim 1 including the steps of: (g) taking a plurality of samples of said papermaking slurry communicated to the stock preparation and filler blending zone; (h) adding predetermined amounts of an electrokinetic charge neutralization agent representing reates of addition of said agent to a respective one of each of said samples and then measuring the TOC values of each of said samples to establish a correlation between the measured TOC values and the rate of addition of said neutralization agent; and determining the rate of adding said neutralization agent in step (d) responsisve to the TOC value obtained in step (c) in accordance to the correlation established in step (h).

4. The process defined in claim 1 wherein the rate of adding said neutralization agent in step (d) is approximately linearly proportional to the measured TOC value obtained in step (c).

5. In an improved papermaking process of the type employing the addition of electrokinetic charge neutralization agents to the papermaking slurry prior to introduction of the slurry to the paper machine, the improvement including the steps of: periodically measuring the TOC value of selected samples of said papermaking slurry to monitor the cationic demand of said slurry; and adjusting the rate of addition of said electrokinetic charge neutralization agents to said slurry proportional to deviations of the measured TOC value of said periodic samples selected from said papermaking slurry and a predetermined TOC value representing a preselected level of cationic demand of the slurry entering the paper machine.

* * * * *